US009844385B2

(12) United States Patent
Dickinson et al.

(10) Patent No.: US 9,844,385 B2
(45) Date of Patent: Dec. 19, 2017

(54) SYSTEMS AND METHODS FOR PROVIDING PRESSURE TO AN EXTREMITY

(71) Applicants: Michael Dickinson, Belfair, WA (US); Robert Carrasca, Seattle, WA (US)

(72) Inventors: Michael Dickinson, Belfair, WA (US); Robert Carrasca, Seattle, WA (US)

( * ) Notice: Subject to any disclaimer, the term of this patent is extended or adjusted under 35 U.S.C. 154(b) by 687 days.

(21) Appl. No.: 14/462,245

(22) Filed: Aug. 18, 2014

(65) Prior Publication Data

US 2015/0051638 A1    Feb. 19, 2015

Related U.S. Application Data

(60) Provisional application No. 61/867,040, filed on Aug. 17, 2013.

(51) Int. Cl.
*A61B 17/132*    (2006.01)

(52) U.S. Cl.
CPC ................ *A61B 17/1322* (2013.01)

(58) Field of Classification Search
CPC ............ A61B 17/1322; A61B 17/1325; A61B 17/1327
USPC ........................................ 606/203
See application file for complete search history.

(56) References Cited

U.S. PATENT DOCUMENTS

| 6,960,223 | B1 | 11/2005 | Ambach |
| 7,582,102 | B2 | 9/2009 | Heinz |
| 2005/0267518 | A1* | 12/2005 | Wright ................ A61B 17/132 606/203 |
| 2013/0296921 | A1* | 11/2013 | Saunders ........... A61B 17/1325 606/203 |

* cited by examiner

*Primary Examiner* — Corrine McDermott
*Assistant Examiner* — Joshua Levine
(74) *Attorney, Agent, or Firm* — Puget Patent; Michael Gibbons (57) ABSTRACT

A high-performance tourniquet for use in rugged environments is disclosed. The tourniquet includes a strap which surrounds an extremity to apply pressure to the extremity. The strap is coupled with a latching mechanism which is operated via a handle to tighten the tourniquet. The ends of the tourniquet are configured to couple via a buckle system enabling a buckle frame to be passed over a buckle tongue. Alternatively, a quick-release stab-lock style fastener buckle may be used to couple the ends of the tourniquet. In either case the tourniquet is designed to enable a victim to personally don the tourniquet and apply the correct pressure. A handle protruding from the outer surface of the tourniquet may be rotated to tighten the tourniquet and apply pressure by moving the tourniquet ends relative to one another. The handle may be pulled outward to quickly undo the pressure.

6 Claims, 10 Drawing Sheets

SYSTEMS AND METHODS FOR PROVIDING PRESSURE TO AN EXTREMITY

PRIORITY CLAIM

This application claims priority from provisional application No. 61/867,040 filed Aug. 17, 2013. The foregoing application is hereby incorporated by reference in its entirety as if fully set forth herein.

FIELD OF THE INVENTION

This invention relates generally to external pressure applicators, and more specifically, to systems and methods for providing pressure to an extremity.

BACKGROUND

Loss of blood is a major cause of death in emergency situations in which the injured person does not have immediate access to medical assistance. The use of a tourniquet to stop blood loss from an injured extremity is a well-known technique for preventing death in these situations. This invention provides a convenient and high quality tourniquet for use to apply pressure to a bodily extremity. The lack of a versatile and high quality tourniquet, which is easy to use, has long presented difficulties. It is desirable to provide a tourniquet capable of being applied by an individual without the aid of another. Another desirable feature is to provide a ruggedized tourniquet which may be used in harsh environments such as may be found on a battlefield, which might include dusty, dirty, or wet conditions that may contaminate the workings of a non-ruggedized tourniquet.

SUMMARY

According to one aspect of the present invention, the tourniquet comprises of a flexible main strap assembly having two elements adapted to engage an extremity of a patient's body, a coupling element, and a handle formation so as to enable the tourniquet to apply pressure to the patient's extremity.

BRIEF DESCRIPTION OF THE DRAWINGS

Embodiments of the present invention are described in detail below with reference to the following drawings.

DETAILED DESCRIPTION

This invention relates generally to external pressure applicators, and more specifically, to systems and methods for providing pressure to an extremity. Specific details of certain embodiments of the invention are set forth in the following description and in FIGS. 1-10 to provide a thorough understanding of such embodiments. The present invention may have additional embodiments, may be practiced without one or more of the details described for any particular described embodiment, or may have any detail described for one particular embodiment practiced with any other detail described for another embodiment.

A tourniquet system is disclosed herein, the tourniquet system configured for providing pressure to an extremity. The tourniquet system provides a convenient and high quality means to apply pressure to a bodily extremity. The present invention comprises of a flexible main strap assembly adapted to engage an extremity of a patient's body, a latching mechanism and a handle formation.

Figure 1:
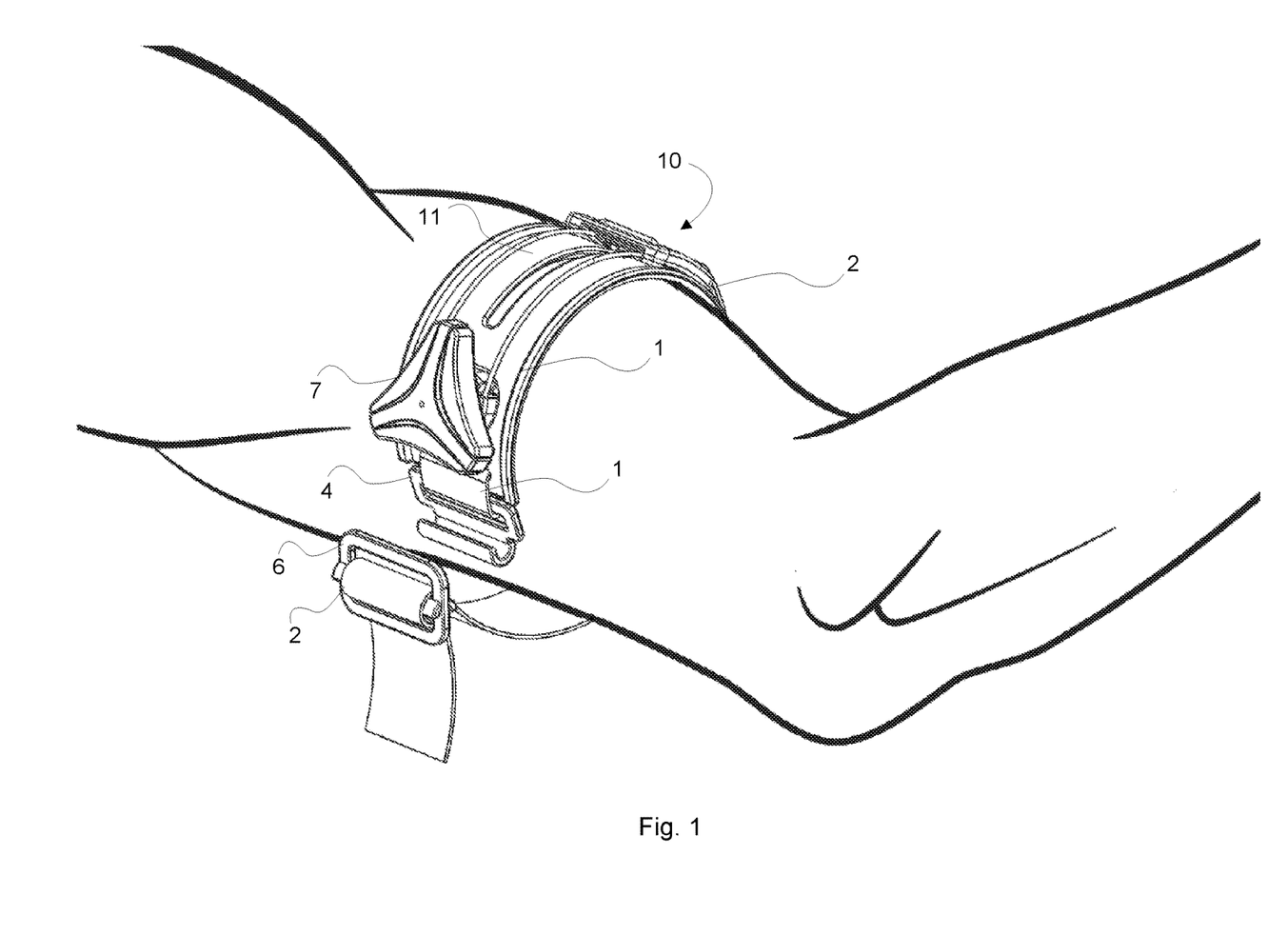
FIG. 1 is an isometric view of the tourniquet system in the unlatched position, in situ, in accordance with an embodiment of the invention.

FIG. 1 is an isometric view of the tourniquet system 10 in the unlatched position, in situ, in accordance with an embodiment of the invention. The tourniquet design enables a victim to individually apply the tourniquet (i.e. without the aid of another) with one hand. The tourniquet includes at least one rigid cuff 11 which provides the tourniquet with sufficient curvature to enable the opened tourniquet to be laid over an arm or other extremity and stay in place while being buckled. The buckle system enabling the tourniquet ends to be coupled may include the buckle-tongue 4 and buckle-frame 6. A first strap 1 is coupled with the buckle-tongue component and a second strap 2 is coupled with the buckle frame component, the first and second straps configured for being positioned relative to one another for tightening the tourniquet via a mechanism which positions the straps.

Figure 2:
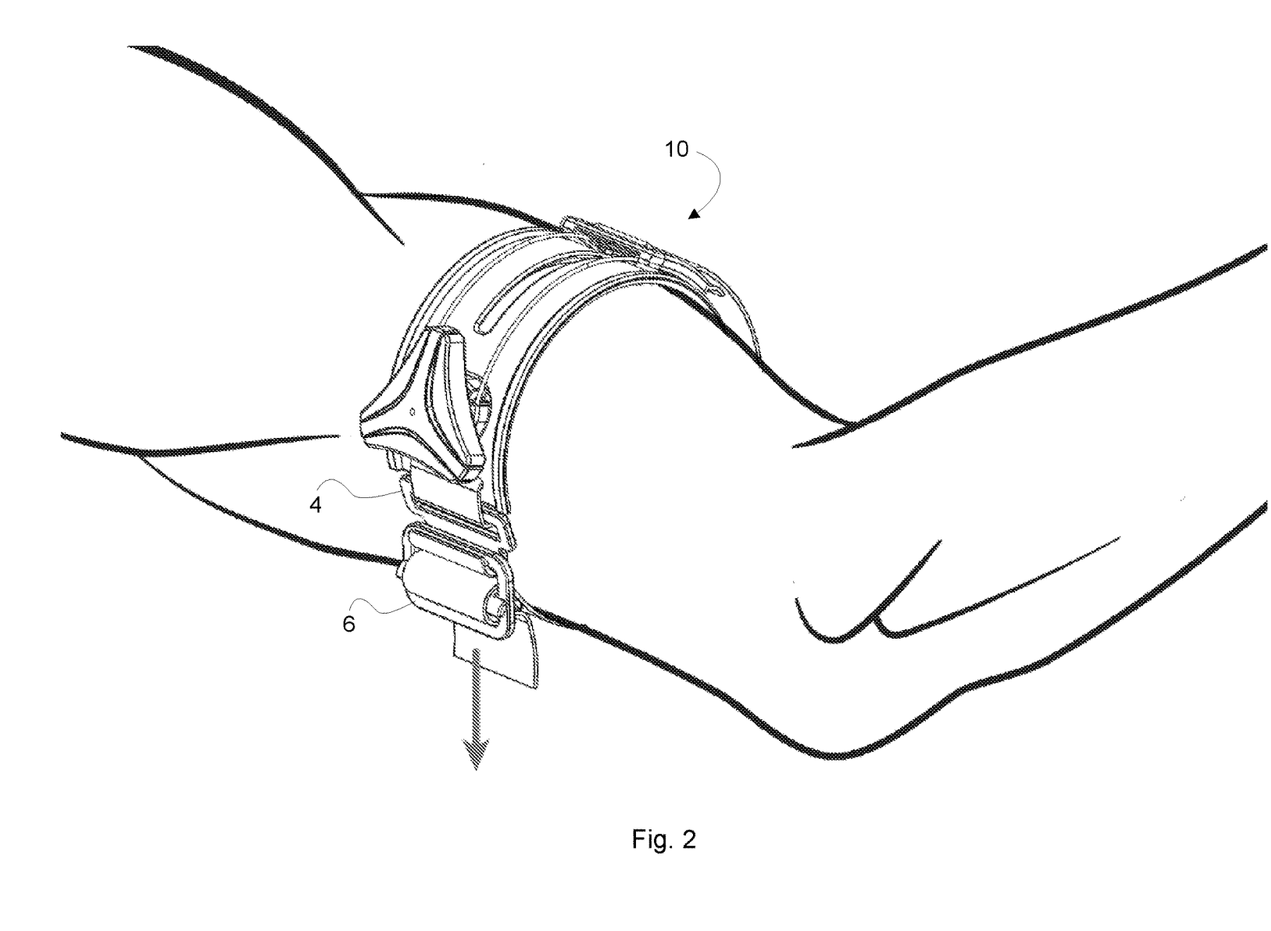
FIG. 2 is an isometric view of the tourniquet system in the latched position, in situ, in accordance with an embodiment of the invention.

FIG. 2 is an isometric view of the tourniquet system 10 in the latched position, in situ, in accordance with an embodiment of the invention. The ends of the tourniquet are latched by sliding an aperture through the buckle-frame 6 over an operative end of the buckle-tongue 4 having a curved profile configured for mating and retaining the buckle-frame. The arrow in FIG. 2 indicates the direction in which the buckle-frame is pulled after being slipped over the operative end of the buckle-tongue.

Figure 3:
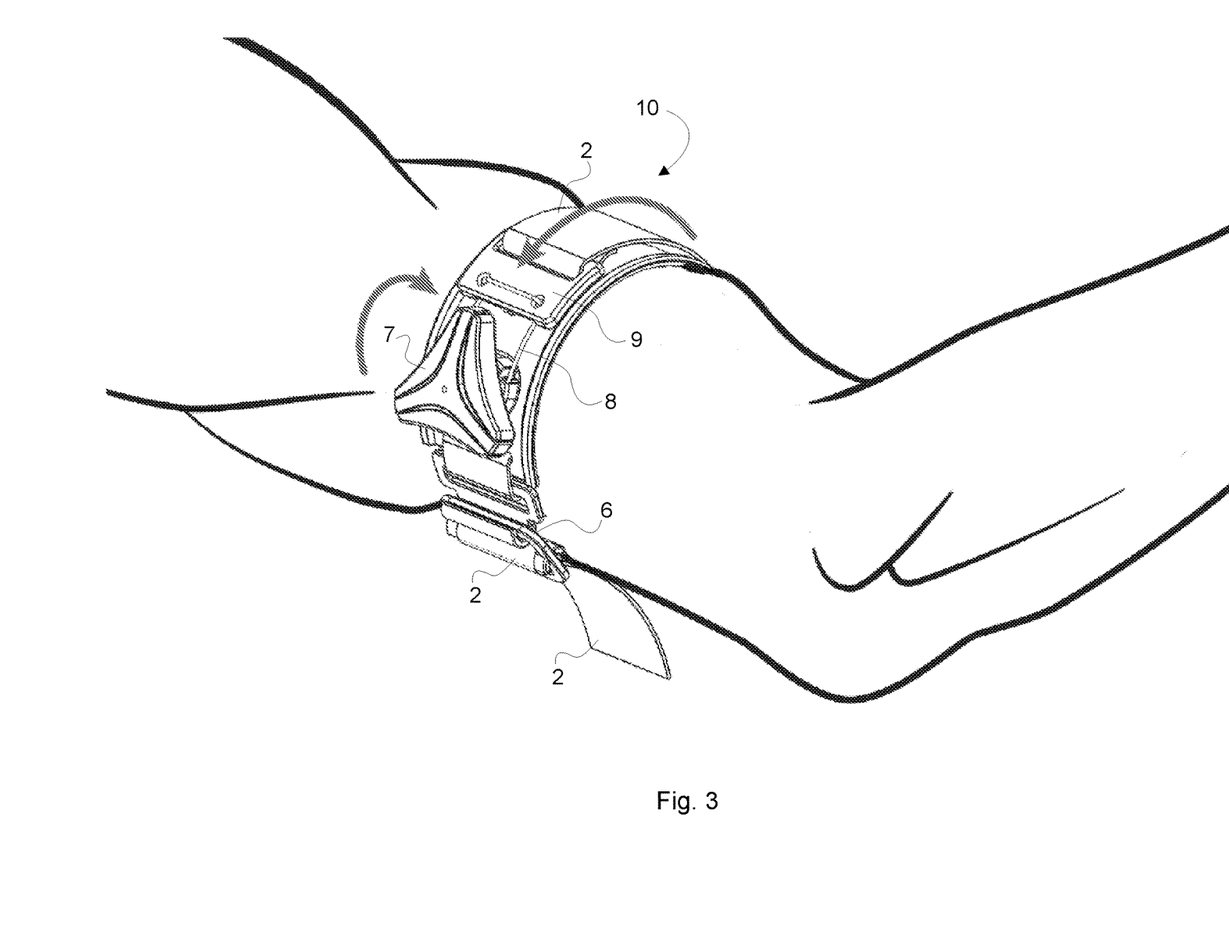
FIG. 3 is an isometric view of the tourniquet system in the latched position, in situ, with arrows indicating strap and handle movements associated with tightening the tourniquet, in accordance with an embodiment of the invention.

FIG. 3 is an isometric view of the tourniquet system 10 in the latched position, in situ, with arrows indicating strap and handle movements associated with tightening the tourniquet, in accordance with an embodiment of the invention. The tourniquet handle formation may be rotated in the direction shown by the arrow to tighten the tourniquet. Tightening the tourniquet via rotating the handle 7 pulls and winds the tension cords 8, which gradually tightens the tourniquet via pulling receptacle plate 9 towards the tourniquet handle. Receptable plate 9 is coupled with a first end of the second strap 1 of the tourniquet; the second end of the second strap is coupled with the buckle-frame. In some embodiments, the tourniquet may be gradually loosened by rotating the handle in the opposite direction.

Figure 4:
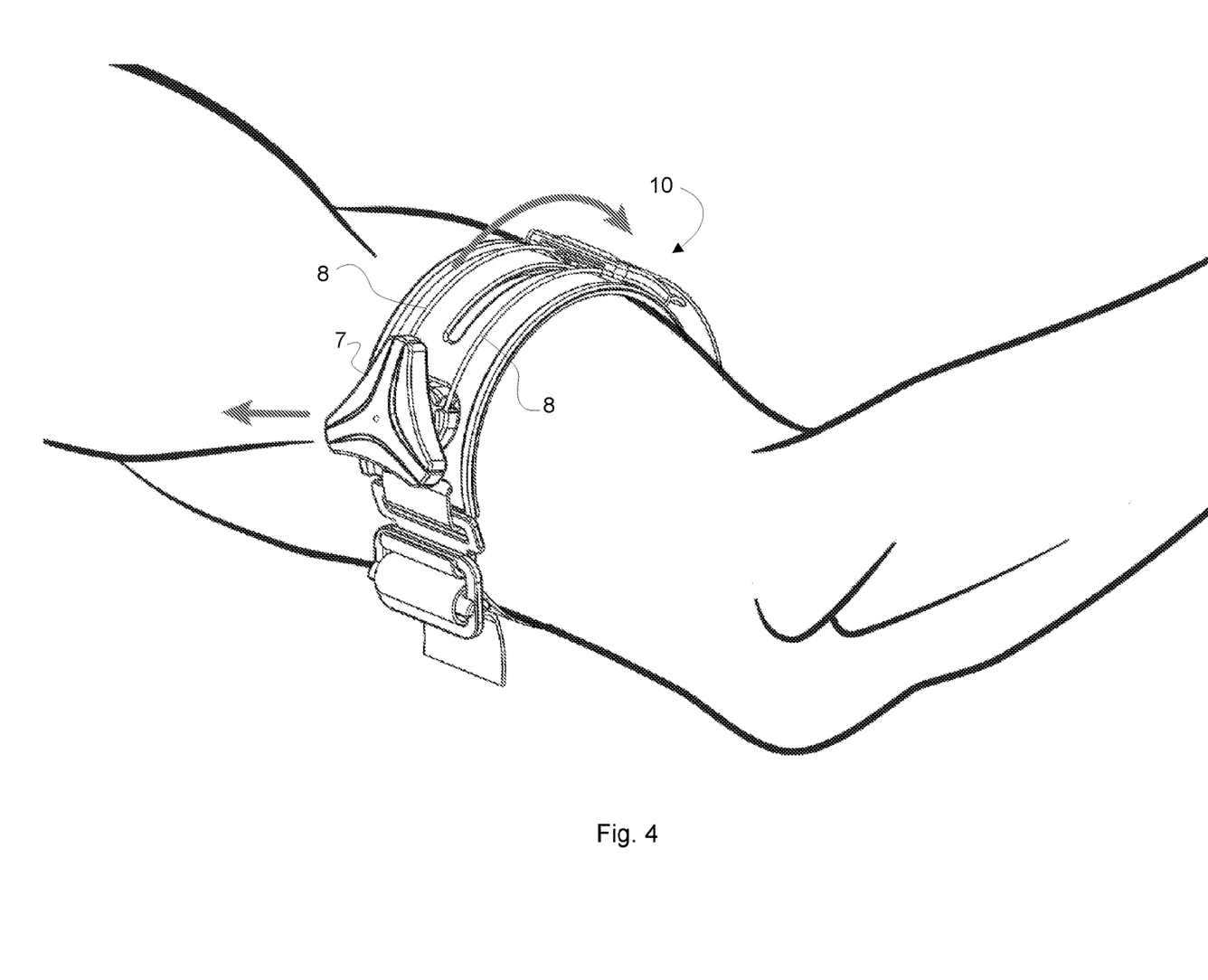
FIG. 4 is an isometric view of the tourniquet system in the latched position, in situ, with arrows indicating strap and handle movements associated with loosening the tourniquet, in accordance with an embodiment of the invention.

FIG. 4 is an isometric view of the tourniquet system 10 in the latched position, in situ, with arrows indicating strap and handle movements associated with loosening the tourniquet, in accordance with an embodiment of the invention. As mentioned above, in some embodiments, the tourniquet may be gradually loosened by rotating handle 7 in the direction opposite of that used to tighten the tourniquet. For more immediate loosening of the tourniquet, the handle may be pulled outward in the direction shown by the arrow. Pulling the handle away from the extremity (i.e. in the direction of the arrow closest to the handle) causes the winding mechanism to disengage such that the tension in the tension cords 8 is immediately released.

FIGS. 5-8 are an isometric view of the tourniquet system 10 in the latched position (FIG. 5); a front view of the tourniquet system 10 in the latched position (FIG. 6); a side view of the tourniquet system 10 in the latched position (FIG. 7); and a side view including a partially cut-away portion of the tourniquet system in the latched position (FIG. 8), all in accordance with various embodiments of the invention. In some embodiments, the tourniquet system 10 may include a sheath (not pictured in FIGS. 5-8 but shown in FIG. 10), a first strap 1, a second strap 2, a strap loop 3, a buckle-tongue 4, a padded element 5, a buckle-frame 6, a handle formation 7, tension cord(s) 8, and a receptacle plate 9.

In the present embodiment, the flexible main strap assembly comprises of two flexible straps 1, 2 each having a first and second longitudinal end. The first and second flexible straps 1, 2 are fabricated from durable, flexible material so as to provide sufficient flexibility to adapt to different profiles of a patient's extremity. In another embodiment, the flexible main straps may be fabricated from nylon.

The first end of the first flexible strap 1 incorporates a rectangular cavity that is sized and positioned to receive a flexible strap loop 3 that attaches the latching mechanism buckle-tongue 4. The width and breadth of the cavity may vary depending on the width and thickness of the flexible strap loop material 3.

In the present embodiment, a tourniquet handle formation 7 is also attached to the first flexible strap 1, at a location adjacent to the flexible strap loop cavity.

In addition, a padded element 5 is bonded to the inside surface of the first flexible strap 1 so as to interface between the first flexible strap 1 and the patient extremity. The padded element 5 comprises of a durable and flexible material having constant thickness. The padded element 5 is intended to assist in distributing pressure uniformly over the patient's extremity. In the present embodiment, the padded element abuts the second edge of the first flexible strap 1 and extends to the base of the tourniquet handle formation 7. In another embodiment, a separate padded element 5 is bonded to the inside surface of the second flexible strap 2.

In the present embodiment, the handle formation 7 comprises of a plurality of lobes to ensure that the tourniquet user's hand will not slip during tightening. In another embodiment, the handle formation 7 (particularly the grip portion) may comprise of a knurled profile, a triangular-shaped grip with arcuate indentations along the three sides, or some other profile that is intended to improve handling while in use.

Figure 8:
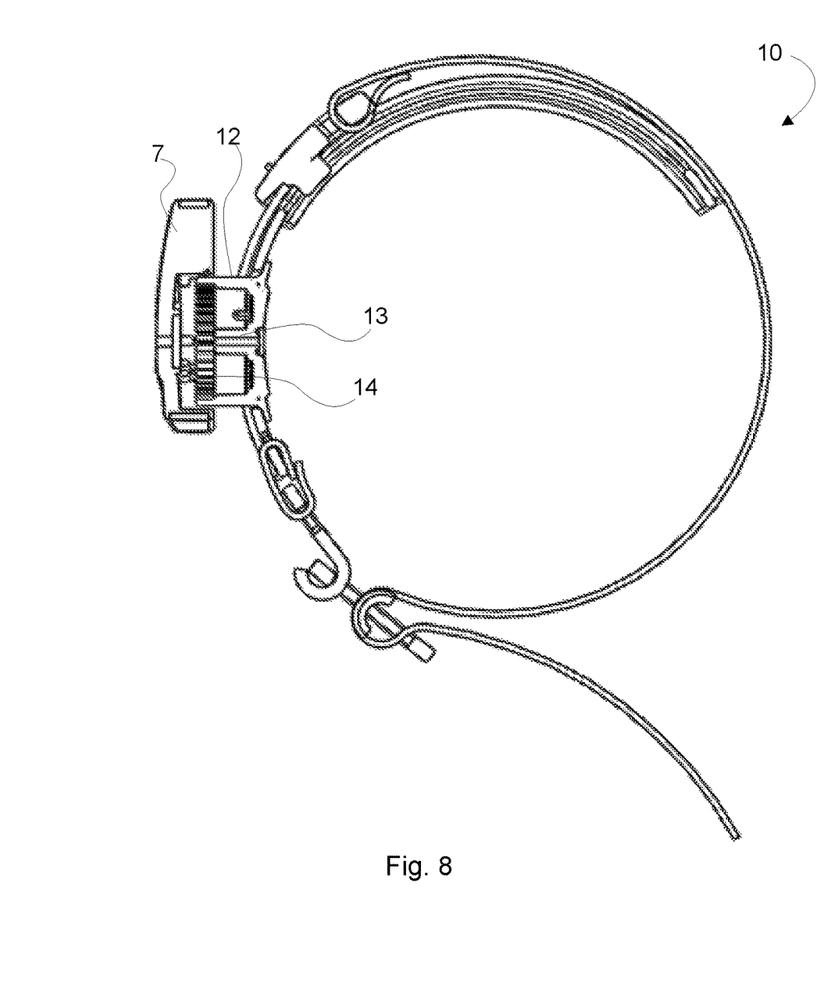
FIG. 8 is a side view including a partially cut-away portion of the tourniquet system in the latched position, in accordance with another embodiment of the invention.

The tourniquet handle formation 7 comprises of a reel frame 12 and a spool shaft 13 extending through the reel frame and rotatably supported about the reel frame. In the present embodiment, the handle formation 7 is mechanically coupled to the spool shaft such that a rotation of the handle causes both tension cords 8 to retract into the spool shaft. The retraction of the tension cords 8 causes the first end of the second flexible strap 2 to move towards the tourniquet handle 7, thereby reducing the enclosed diameter of the tourniquet system, which in turn applies pressure to a patient extremity when fitted. A toothed gear and ratcheting arrangement 14 is disposed about the spool shaft, permitting the tourniquet to stay tight as the handle is rotated. Upon the handle being pulled outward, the toothed gear pops out of the ratchet arrangement facilitating immediate loosening of the tension cords (coarse loosening). In some embodiments, the ratchet arrangement is configured for enabling fine control of loosening of the tourniquet via rotation of the handle in the opposite direction.

The first and second flexible straps are joined at one location by a receptacle plate 9. The receptacle plate 9 comprises of a rectangular plate having constant thickness and a shallow curved profile. In the present embodiment, the curved profile is designed to conform to the tourniquet profile when applied to a patient extremity. In another embodiment, the receptacle plate may be flat. The receptacle plate 9 further comprises of two circular holes, which are sized and positioned to receive the tourniquet system tension cords 8 that retract and extend to and from the tourniquet handle formation 7. The receptacle plate 9 further comprises of a rectangular cavity that is sized and positioned to receive the first end of the second flexible strap 2.

In the present embodiment, the receptacle plate 9 is attached to the first flexible strap 1 through the tension cords 8 that spool into the handle formation 7. In another embodiment, the receptacle plate 9 further comprises of integral guide located on its first and second longitudinal sides. FIG. 8. The integral guide is sized and positioned to envelope the cross-sectional profile of the first flexible strap 1 so as to provide a degree of translational guidance to the second flexible strap 2 while it overlaps the first flexible strap 1.

In addition, the first end of the second flexible strap 2 is also attached to the receptacle plate 9. The first end of second flexible strap 2 passes through the rectangular cavity of the receptacle plate 9 and is then fixed onto an overlapping portion of itself, subsequently creating a loop. The loop thereby provides a rigid translational connection between the receptacle plate 9 and second flexible strap 2.

Furthermore, the tourniquet system further comprises of a latching mechanism. In the present embodiment, the latching mechanism comprises of a curved buckle tongue 4 and a rectangular buckle frame 6. In the present embodiment, the curved buckle tongue 4 is attached to the first end of the first flexible strap 1 by a flexible strap loop 3. An advantage of the flexible strap loop 3 is that it provides translational fixity between the buckle-tongue 4 and first flexible strap 1, while allowing the buckle-tongue 4 to rotate freely about the first flexible strap edge 1.

Figure 7:
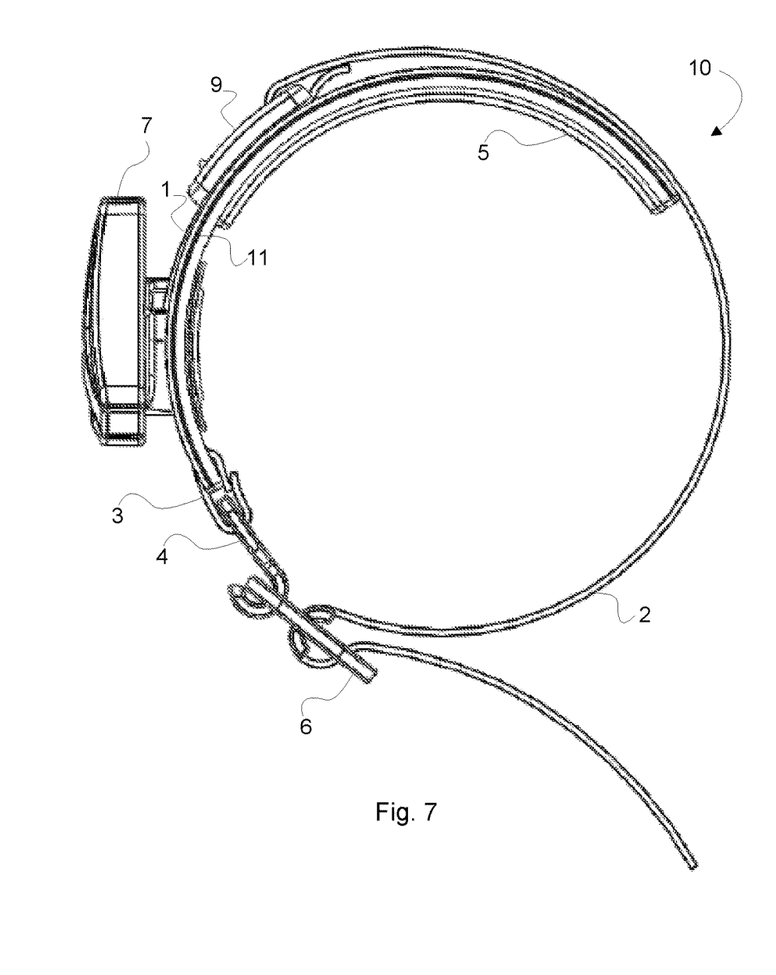
FIG. 7 is a side view of the tourniquet system in the latched position, in accordance with an embodiment of the invention.

The rectangular buckle frame 6 is attached to the second end of the second flexible strap 2. The rectangular buckle frame 6 comprises of a flat plate, having constant thickness, and further comprising of two rectangular cavities, which are designed to receive the second end of the second flexible strap 2 and the buckle-tongue 4. The second end of the second flexible strap 2 is looped through the first and second rectangular cavities of the rectangular buckle frame 6 in order to create a friction joint. (FIG. 7, 8). The length of the second flexible strap 2 may be reduced or increased by passing a greater and lesser length of the second flexible strap through the rectangular buckle frame cavities.

Figure 5:
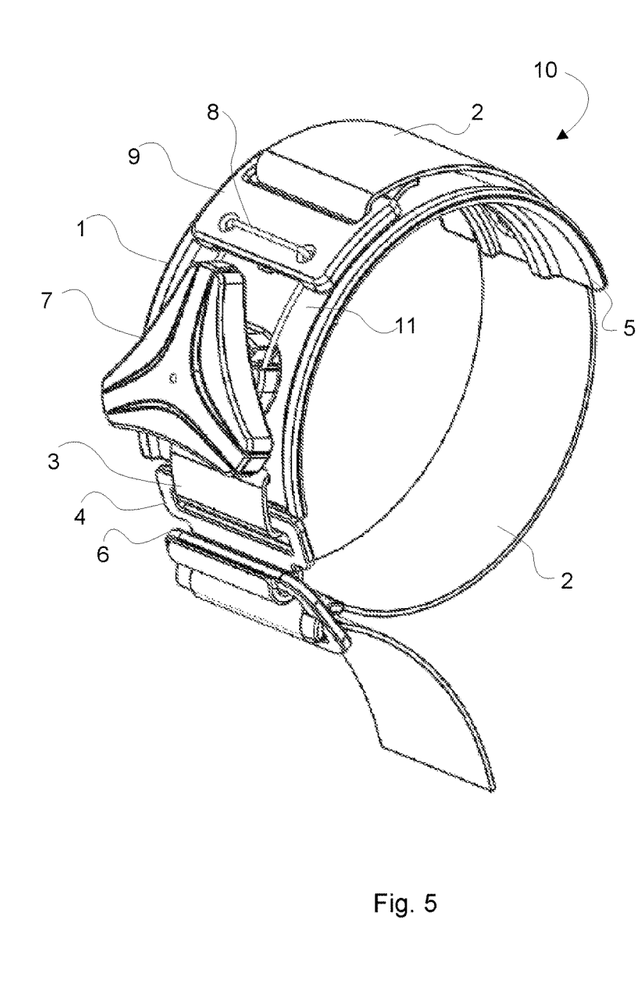
FIG. 5 is an isometric view of the tourniquet system in the latched position, in accordance with an embodiment of the invention.
Figure 6:
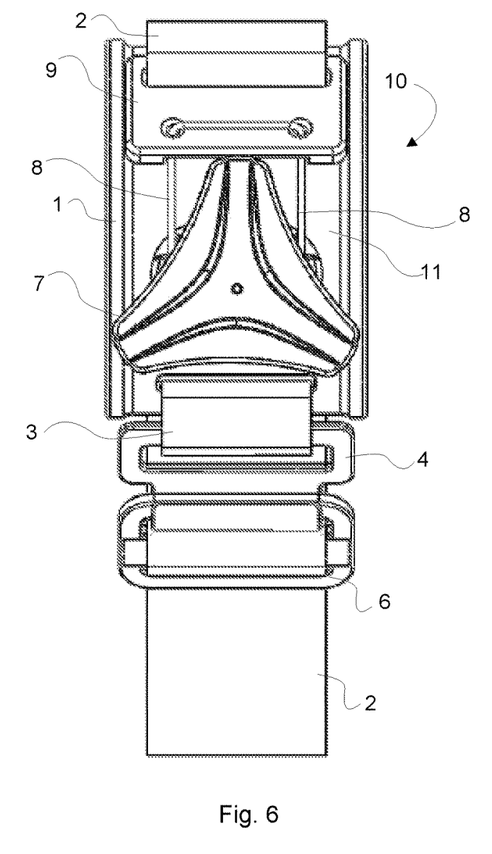
FIG. 6 is a front view of the tourniquet system in the latched position, in accordance with an embodiment of the invention.

The second component of the latching mechanism is the buckle-tongue 4. The buckle tongue 4 comprises of a plate, having constant thickness, a rectangular cavity and a lipped operative edge. (FIG. 5, 8). The rectangular cavity is sized and positioned to receive the flexible strap loop 3. The width and breath of the rectangular cavity may vary depending on the width and thickness of the flexible strap loop material 3. The curvature of the operative edge of the buckle-tongue 4 forms a 180 degree semi-circle so as to improve connectivity of the latching mechanism when the buckle-tongue 4 and buckle-frame 6 are engaged. An added advantage of the buckle tongue profile is that it will prevent the latching mechanism from disconnecting when the tourniquet assembly is placed on a patient upside down. In another embodiment, the operative edge of the buckle-tongue 4 may be square, beveled, or some other profile that provides the required connectivity.

In the present embodiment, the latching mechanism is engaged when the concave surface of the buckle-tongue 4 passes through and engages the adjacent inside surface of the buckle frame cavity 6.

Figure 9:
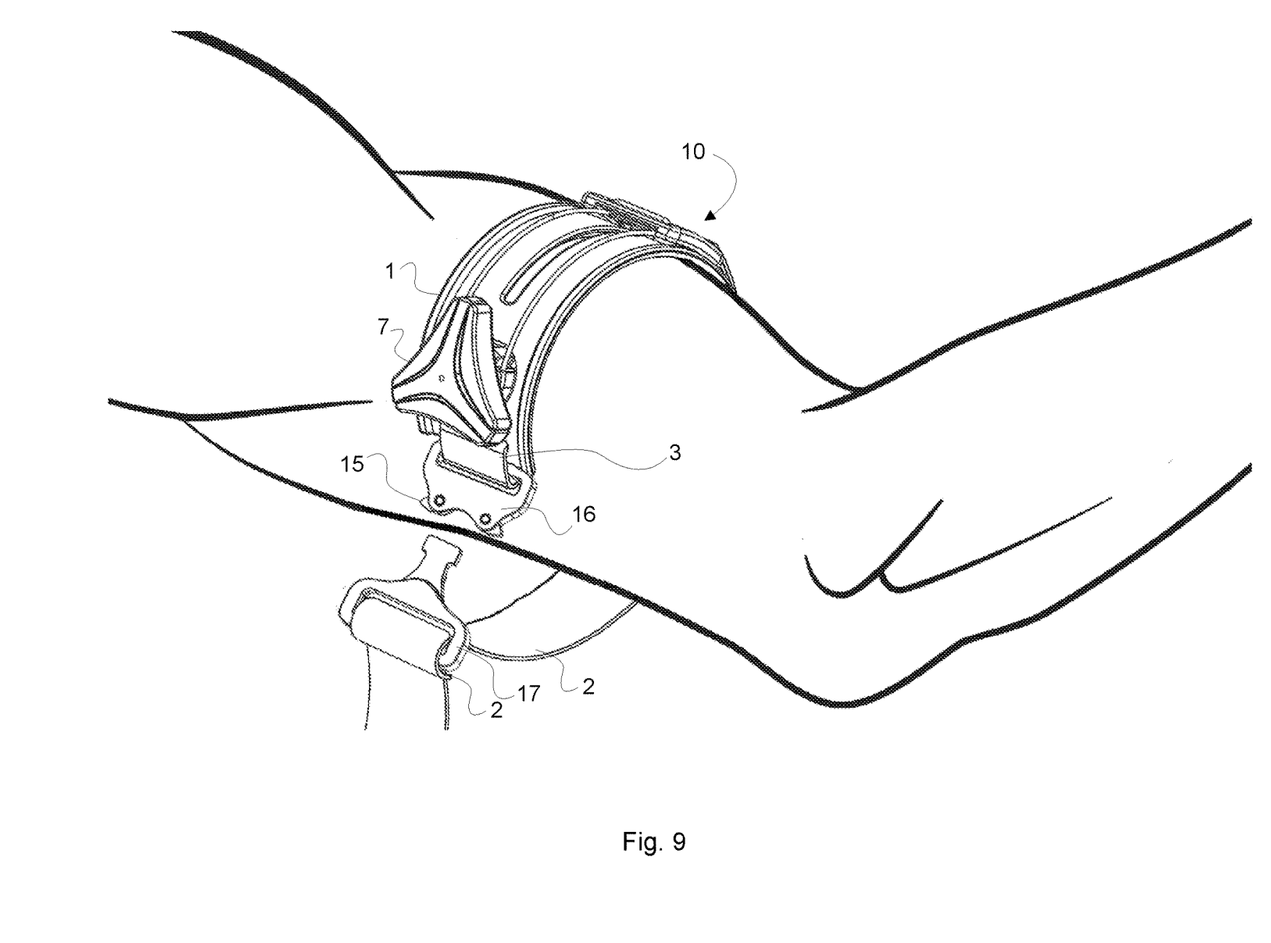
FIG. 9 is an isometric view of an alternate embodiment of the tourniquet in the unlatched position, in situ, in accordance with an embodiment of the invention.

FIG. 9 is an isometric view of an alternate embodiment of the tourniquet 10 in the unlatched position, in situ, in accordance with an embodiment of the invention. In an alternate arrangement, the buckle-tongue and buckle-frame are replaced with a stab-lock style of buckle, the stab-lock style buckle including a female connector 16 and a male connector 17. The female connector may be attached via the strap loop 3 to the first flexible strap 1. The male connector may be attached to the second flexible strap 2 via the strap being threaded through and around the male connector. The female connector includes release tabs 15. In this embodiment, the proximal end of the male connector can be inserted into the female connector. The female connector includes a mechanism which locks around the fat part of the proximal end of the male connector. The release tabs 15 may be used to disconnect the male and female connectors of the stab-lock buckle.

Figure 10:
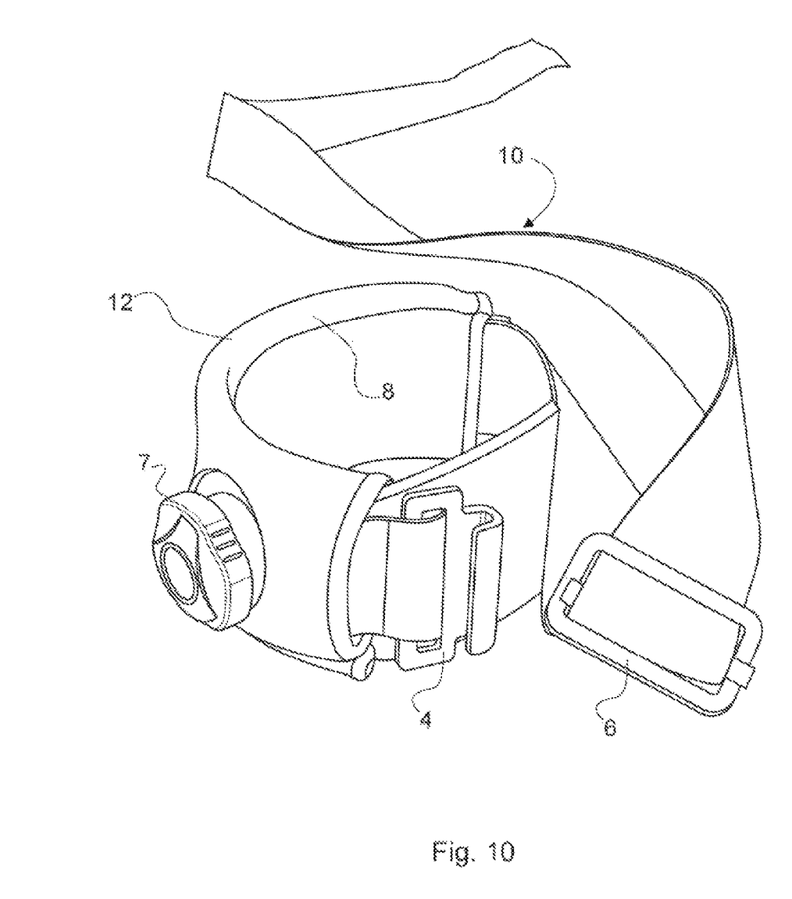
FIG. 10 is an isometric view of an embodiment of the tourniquet featuring a sheath installed for protecting certain working components of the device, in accordance with an embodiment of the invention.

FIG. 10 is an isometric view of an embodiment of the tourniquet 10 featuring a sheath 12 installed for protecting certain working components of the device, in accordance with an embodiment of the invention. It should be understood that a sheath is positioned over portions of the tourniquet to protect the interior mechanics of the system. The sheath would surround the tourniquet, with only the handle 7, the buckle system components (buckle-tongue 4 and buckle-frame 6), and distal portions such as the straps threaded through the buckle system components exposed to the elements. The sheath contributes to the rugged nature of the tourniquet enabling use in harsh environments such that dust, dirt, liquids, or other contaminants are unable to penetrate the inner workings of the tourniquet causing it to fail.

While preferred and alternative embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A tourniquet, comprising:
   a first flexible strap;
   a second flexible strap;
   a first buckle component coupled with the first flexible strap;
   a rigid cuff coupled with the first flexible strap, the rigid cuff including at least one rigid curvature portion defining a recess for receiving a portion of the body to enable the tourniquet to stay in place about the portion of the body while the tourniquet is buckled;
   a receptacle plate coupled with the second flexible strap at a first end of the second flexible strap;
   a second buckle component coupled with the second flexible strap at a second end of the second flexible strap;
   a rotatable handle formation coupled with the first flexible strap, the rotatable handle formation including at least:
      a reel frame;
      a spool shaft extending through the reel frame, the spool shaft rotatably supported about the reel frame;
      a handle disposed at an end of the spool shaft exterior to the reel frame;
      a toothed gear; and
      a ratchet, the toothed gear being engaged with the ratchet when the handle is pressed into the reel frame and disengaging from the ratchet upon the handle being pulled away from the reel frame, the toothed gear and ratchet being engaged or disengaged via the handle operable to enable fine or coarse loosening of the tourniquet;
   two or more tension cords at least partially wound about the spool shaft and coupled with the receptacle plate, wherein rotation of the handle and spool shaft causes the tension cords to retract into the spool shaft, reducing a diameter of the tourniquet when the first and second buckle components are coupled; and
   a sheath.

2. The tourniquet of claim 1, wherein the first buckle component coupled with the first flexible strap comprises:
   the first buckle component coupled with the first flexible strap via a flexible strap loop.

3. The tourniquet of claim 1, wherein the second buckle component coupled with the second flexible strap at a second end of the second flexible strap comprises:
   the second buckle component coupled with the second flexible strap at a second end of the second flexible strap via at least a portion of the second flexible strap being threaded through a portion of the second buckle component.

4. The tourniquet of claim 1, wherein the rotatable handle formation including at least a spool shaft comprises:
   the rotatable handle formation including at least a spool shaft configured for retracting at least a portion of the one or more tension cords upon a grip portion of the rotatable handle formation being rotated, the retracting at least a portion of the one or more tension cords operable to pull the receptacle plate towards the female stab-lock buckle and tighten the tourniquet.

5. The tourniquet of claim 1, wherein the rotatable handle formation including at least a spool shaft comprises:
   the rotatable handle formation including at least a toothed gear and ratcheting arrangement configured for loosening tension of the tension cords upon a grip portion of the rotatable handle formation being pulled away from the tourniquet.

6. The tourniquet of claim 1, wherein the rotatable handle formation including at least a spool shaft comprises:

the rotatable handle formation including at least a triangular-shaped grip portion with arcuate indentations along the three sides.

* * * * *